United States Patent
Aldrich et al.

(10) Patent No.: US 6,689,724 B2
(45) Date of Patent: Feb. 10, 2004

(54) ANTIOXIDANTS AND ANTIOXIDANT BOOSTERS CAPABLE OF PRODUCING HYDROPEROXYL RADICALS

(75) Inventors: Haven S. Aldrich, Baton Rouge, LA (US); Richard H. Schlosberg, Bridgewater, NJ (US); Stanley J. Brois, Westfield, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/855,125

(22) Filed: May 14, 2001

(65) Prior Publication Data

US 2002/0082174 A1 Jun. 27, 2002

Related U.S. Application Data (63) Continuation-in-part of application No. 08/713,420, filed on Sep. 13, 1996, now abandoned.

(51) Int. Cl.[7] ............................................. C10M 133/48
(52) U.S. Cl. ....................................................... 508/278
(58) Field of Search ................................. 508/270, 486, 508/277, 278

(56) References Cited

U.S. PATENT DOCUMENTS 4,849,123 A * 7/1989 Tipton et al. .................. 252/74

FOREIGN PATENT DOCUMENTS

| WO | WO 96/28525 | 9/1996 | ........ C10M/105/40 |
| WO | WO 98/11179 | 3/1998 | ........ C10M/105/40 |
| WO | WO 98/11181 | 3/1998 | ........ C10M/133/00 |

\* cited by examiner

*Primary Examiner*—Cephia D. Toomer
(74) *Attorney, Agent, or Firm*—Paul E. Purwin; Joseph C. Wang

(57) ABSTRACT

An antioxidant which comprises a primary aliphatic hydroxyl group linked to an organic backbone such that upon oxidation a hydroperoxyl moiety capable of boosting the efficacy of free radical scavengers and hydroperoxide decomposer type antioxidants is generated in situ. The antioxidant is preferably a high hydroxyl polyol ester having a hydroxyl number ranging from about 30 to about 180 which ester is the reaction product of polyol and an acid which is at least fifty percent branched carboxylic acid, wherein the unconverted hydroxyl group is reacted with a facile leaving group, thereby producing free —$CH_2OH$ groups upon hydrolysis or oxidation.

11 Claims, 2 Drawing Sheets

ANTIOXIDANTS AND ANTIOXIDANT BOOSTERS CAPABLE OF PRODUCING HYDROPEROXYL RADICALS

This application is a continuation-in-part of U.S. Ser. No. 08/713,420, filed Sep. 13, 1996, now abandoned.

The present invention generally relates to enhanced efficiency antioxidants and antioxidant boosters. The unique antioxidants are preferably formed such that they contain a predetermined amount of unconverted hydroxyl groups which produce the hydroperoxyl radical or moiety (HOO.) upon oxidation. The hydroperoxyl radical reacts with alkoxyl radicals (RO.) or alkylperoxyl radicals (ROO.) to produce stable intermediates and molecular oxygen. The antioxidants of the present invention can be used by themselves, grafted onto conventional antioxidants to act as antioxidant boosters, or grafted onto other materials such as mineral oils, polyol esters, polyalpha olefin base stocks, fuels, oligomers and polymers so as to provide antioxidant protection.

BACKGROUND OF THE INVENTION

Lubricants in commercial use today are prepared from a variety of natural and synthetic base stocks admixed with various additive packages and solvents depending upon their intended application. The base stocks typically include mineral oils, highly refined mineral oils, poly alpha olefins (PAO), polyalkylene glycols (PAG), phosphate esters, silicone oils, diesters and polyol esters.

Polyol esters have been commonly used as base stocks in lubricant application where thermal and oxidative stability are critical. Despite their inherent thermal/oxidative stability as compared with other base stocks (e.g., mineral oils, polyalpha olefins, etc.), even these synthetic ester lubricants are subject to oxidative degradation and cannot be used, without further modification, for long periods of time under oxidizing conditions. It is known that this degradation is related to oxidation and hydrolysis of the ester base stock.

Conventional synthetic polyol ester lubricant oil formulations require the addition of antioxidants (also known as oxidation inhibitors). Antioxidants reduce the tendency of the ester base stock to deteriorate in service in which deterioration can be evidenced by the products of oxidation such as sludge and varnish-like deposits on the metal surfaces, and by viscosity and acidity growth. Such antioxidants include arylamines (e.g., dioctyldiphenylamine (V-81) and phenylalphanaphthylamine), and the like.

Frequently replacing the lubricant oil or adding an antioxidant thereto to suppress oxidation increases the total cost of maintaining the engine or machine. It would be most desirable to either enhance the efficiency of conventional antioxidants (i.e., provide increased antioxidant potency in formulated products) or produce an ester base stock which exhibits substantially enhanced thermal/oxidative stability compared to conventional synthetic ester base stocks, and wherein the ester base stock does not require frequent replacement due to decomposition (i.e., oxidation degradation). It would also be economically desirable to eliminate or reduce the amount of antioxidant which is normally added to such lubricant base stocks.

Upon thermal oxidative stress a weak carbon hydrogen bond cleaved ultimately resulting in an unstable alkylperoxyl radical on the ester. The role of conventional antioxidants is to transfer a hydrogen atom to the unstable carbon radical and effect a "healing" of the radical. The following equation demonstrates the effect of antioxidants (AH):

$$AH + ROO. \rightarrow A. + ROOH$$

The antioxidant molecule is converted into a radical, but this radical (A.) is far more stable than that of the ester-based system. Thus, the effective lifetime of the ester is extended. When the added antioxidant is consumed, the ester radicals are not healed and oxidative degradation of the polyol ester composition occurs. One measure of relative thermal/oxidative stability well known in the art is the use of high pressure differential scanning calorimetry (HPDSC).

HPDSC has been used to evaluated the thermal/oxidative stabilities of formulated automotive lubricating oils (see J. A. Walker, W. Tsang, SAE 801383), for synthetic lubricating oils (see M. Wakakura, T. Sato, Journal of Japanese Petroleum Institute, 24 (6), pp. 383–392 (1981)) and for polyol ester derived lubricating oils (see A. Zeeman, Thermochim, Acta, 80(1984)1). In these evaluations, the time for the bulk oil to oxidize was measured; this is the induction time. Longer induction times have been shown to correspond to oils having higher concentrations of antioxidants or correspond to oils having more effective antioxidants or at a fixed level of a given antioxidant, have been shown to correspond to oils having intrinsically more stable base stocks. For automotive lubricants, higher induction times have been correlated with viscosity break point times.

The use of HPDSC as described herein provides a measure of stability through oxidative induction times. A polyol ester can be blended with a constant amount of dioctyl diphenylamine which is an antioxidant. This fixed amount of antioxidant provides a constant level of protection for the polyol ester base stock against bulk oxidation. Thus, oils tested in this manner with longer induction times have greater resistance to oxidation. For the high hydroxyl esters of the present invention in which no antioxidant has been added, the longer induction times reflect the greater stability of the polyol ester high hydroxyl molecules by and also the natural intrinsic antioxidancy of the esters due to the unesterified —$CH_2OH$ groups.

The present inventors have developed a unique polyol ester composition having enhanced thermal/oxidative stability when compared to conventional synthetic polyol ester compositions. This was accomplished by synthesizing a polyol ester composition from a polyol and branched and/or linear carboxylic or aromatic acid in such a way that it has a substantial amount of unconverted —$CH_2OH$ groups. Having a highly branched polyol ester backbone enhances the ability of the high hydroxyl ester to act similarly to an antioxidant, i.e., cause the thermal/oxidative stability of the novel polyol ester composition to drastically increase, as measured by high pressure differential scanning calorimetry (HPDSC). This selectively branched polyol ester composition restricts the mechanisms by which the non-$CH_2OH$ portion of the high hydroxyl ester oxidizes and thereby provides an intramolecular mechanism which is capable of scavenging alkoxide and alkyl peroxide radicals, thereby substantially reducing the rate at which oxidative degradation can occur.

The thermal and oxidative stability which is designed into the novel polyol ester compositions of the present invention eliminates or reduces the level of antioxidant which must be added to a particular lubricant, thereby providing a substantial cost savings to lubricant manufacturers. Furthermore, the novel high hydroxyl polyol esters of the present invention are capable of decreasing the level of other antioxidants required when they are grafted to other formulated products including lubricants, fuels, oligomers and polymers, thus potentially reducing the cost of formulation to achieve desired performance targets.

Another problem of conventional formulations is that the ability to dissolve conventional antioxidants in the respective base stock varies widely and in some instances the use of the selected antioxidants is prohibited due to solubility limitations. The present invention also offers a means of incorporating additives into formulations that may be poorly soluble by attaching them through conventional hydrocarbon bonds to the additive in question. The high hydroxyl ester thus provides not only solubility but provides antioxidancy to the additive in question.

The high hydroxyl polyol esters of the present invention, when grafted onto oligomers, polymers or the like are capable of providing the enhancement of oxidation stability without the potential debits associated with conventional antioxidants that are known to produce color bodies, a significant debit for selected polymer applications.

The present invention also provides many additional advantages which shall become apparent as described below.

SUMMARY OF THE INVENTION

The antioxidant of the present invention is preferably a unique polyol ester having unconverted hydroxyl groups from the reaction product of a polyol with a branched and/or linear carboxylic or aromatic acid, thereby allowing the unconverted —$CH_2OH$ groups to form the hydroperoxyl moiety (HOO.) upon oxidation. This antioxidant comprises a primary aliphatic hydroxyl group linked to an organic backbone such that upon oxidation a hydroperoxyl moiety capable of boosting the efficacy of free radical scavengers and hydroperoxide decomposer type antioxidants is generated in situ.

Antioxidants that are covered by the present invention include the general class of polyol esters, phenols, aromatic amines, phosphites, and sulfur containing antioxidants, as well as any conventional antioxidants that function as free radical inhibitors or hydroperoxide decomposers, provided that these antioxidants contain an unconverted —$CH_2OH$ group which is capable of forming a hydroperoxyl radical or moiety (HOO•). Depending upon the structure of the acid used, the resultant ester product can function as either an antioxidant or an antioxidant booster.

The antioxidant comprises the reaction product of: a branched or linear alcohol having the general formula $R(OH)_n$, wherein R is an aliphatic or cyclo-aliphatic group having from about 2 to 20 carbon atoms and n is at least 2; and at least one branched or linear carboxylic acid which has a carbon number in the range between about $C_2$ to $C_{20}$; wherein said antioxidant has a hydroxyl number greater than about 30 to about 180 and preferably between about 40 and 120. The unconverted hydroxyl group of this antioxidant is preferably reacted with a facile leaving group, thereby producing free —$CH_2OH$ groups upon hydrolysis or oxidation of the chemically protected derivative.

Alternatively, the antioxidant of the present invention includes the modification of general antioxidants (AH) through grafting reactions that result in new antioxidants which produce free —$CH_2OH$ groups upon hydrolysis and/or oxidation. Such antioxidants formed through grafting of general antioxidants (AH) to form a reaction product comprising an unconverted —$CH_2OH$ moiety. The preferred reaction product comprises the reaction of YH with a polyol diacrylate, wherein Y is selected from the group consisting of: RS, $R_2N$, $(RO)_2PHO$, phenols and mixtures thereof; provided that RS is part of a sulfur containing antioxidant, $R_2N$ is an aromatic amine or an alkyl amine antioxidant, and $(RO)_2PHO$ is a phosphite antioxidant.

Alternatively, the antioxidant of the present invention also includes antioxidants that do not contain any free hydroxyl groups nor any chemical bonds that would produce the —$CH_2OH$ moiety upon hydrolysis, but which do produce the hydroxyl group upon oxidation. Such an antioxidant would also have boosted antioxidant capacity due to the subsequent oxidation reaction of the —$CH_2OH$ moieties to yield the hydroperoxyl moiety (HOO.). The hydroperoxyl radical or moiety can then react with alkylperoxyl radicals or with alkylhydroperoxyl radicals to produce stable intermediates (e.g., ROOH) and molecular oxygen. Such antioxidant can be derived from the reaction product of: (1) tris (hydroxymethyl)aminomethane and formaldehyde, thereby producing 1-aza-3,7-dioxa-bicyclo[3.3.0]octyl-5-methanol; (2) tris (hydroxymethyl)aminomethane and cyclohexanone, thereby producing 2,2-pentamethylene-1,3-oxazolidine-4,4-dimethanol; (3) tris (hydroxymethyl)aminomethane and a linear or branched carboxylic acid, thereby producing amides having the general formula:

wherein R is a linear or branched alkyl chain derived from the reaction product of a linear or branched acid with tris (hydroxymethyl)aminomethane; and (4) tris (hydroxymethyl)aminomethane and a linear or branched carboxylic acid, thereby producing substituted oxazolines having the general formula:

wherein R is a linear or branched alkyl chain derived from said linear or branched carboxylic acid.

The unique high hydroxyl polyol esters antioxidants of the present invention, when grafted onto mineral oils, polyol esters, polyalpha olefin base stocks, fuels, oligomers and polymers can increase the oxidation stability of those materials as well.

The present invention also includes a lubricant which is prepared from at least one synthetic polyol ester composition having unconverted hydroxyl groups as set forth immediately above and a lubricant additive package. Additionally, a solvent may also be added to the lubricant, wherein the lubricant comprises about 60–99% by weight of the synthetic polyol ester composition, about 1 to 20% by weight the additive package, and about 0 to 20% by weight of the diluent.

The lubricant is preferably one selected from the group consisting of: crankcase engine oils, two-cycle engine oils, catapult oils, hydraulic fluids, drilling fluids, turbine oils, greases, compressor oils, gear oils, and functional fluids.

The additive package comprises at least one additive selected from the group consisting of: viscosity index improvers, corrosion inhibitors, oxidation inhibitors, dispersants, lube oil flow improvers, detergents and rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, and additive solubilizers.

Still other lubricants can be formed according to the present invention by blending this unique synthetic high hydroxyl polyol ester composition of the present invention and at least one additional base stock selected from the group consisting of: mineral oils, highly refined mineral oils, poly alpha olefins, polyalkylene glycols, phosphate esters, silicone oils, diesters and polyol esters. The synthetic polyol ester composition is blended with the additional base stocks in an amount between about 1 to 50 wt. %, based on the total blended base stock, preferably 1 to 25 wt. %, and most preferably 1 to 15 wt. %.

DESCRIPTION OF THE PREFERRED EMBODIMENTS

High hydroxyl number esters (i.e., hydroxyl numbers between greater than about 30 to about 180) are preferably derived from selected carboxylic acids, such as 3,5,5-trimethylhexanoic acid or 2-ethylhexanoic acid and combinations thereof, and have the capability of scavenging radicals, such as alkylperoxyl radicals and alkylhydroperoxyl radicals. In a preferred embodiment, the hydroxyl number of the high hydroxyl ester ranges from greater than about 40 to about 120, and most preferably greater than about 50 to about 100. As such, when such high hydroxyl esters are subjected to oxidation conditions using HPDSC experiments as shown hereafter, they tend to resist oxidation because they have intrinsic antioxidancy.

Furthermore, the same esters have the capability of providing oxidation stability to other materials such as mineral oils, polyol esters, polyalpha olefin base stocks, fuels, oligomers and polymers by providing antioxidant protection. The advantage of such high hydroxyl polyol esters is that their use as antioxidants can reduce the dependency on other antioxidants such as phenols or aromatic amines.

These high hydroxyl polyol esters can also enhance the performance of conventional antioxidants such as phenols or diphenylamines when used as a diluent solvent. The free radical scavenging of the high hydroxyl esters synergistically compliments that of the conventional antioxidants and thus boosts their performance. In addition, because of their polarity, the high hydroxyl esters have the potential of increasing the solubility of additives used to formulate lubricants and fuels. The reaction of the high hydroxyl esters with other additives, some of which may be antioxidants themselves, can increase the oil solubility of those additive systems and simultaneously provide a boosted antioxidancy to the formulation.

The present invention of using high hydroxyl esters as antioxidants is consistent with the mechanism shown below. The products of oxidation were used to construct the degradation pathways shown below which demonstrate how the high hydroxyl esters degrades during oxidation. The performance of the high hydroxyl ester as an antioxidant depends upon the high hydroxyl ester itself degrading oxidatively. The key to the intrinsic antioxidancy is the formation of the hydroperoxyl moiety (HOO.). As shown below the reaction of the hydroperoxyl radical with other reaction products that are formed result in the inhibition of the oxidation reaction. The inhibition of oxidation is associated with interfering with the chain propagating step which is normally responsible for the rapid propagation and oxidative degradation. A further key to an effective antioxidant is that the rate of generation of the hydroperoxyl moiety (HOO.) needs to exceed the rate of the oxidation mechanism responsible for the degradation of the non-CH$_2$OH portion of the high hydroxyl esters.

The following reactions demonstrate the inhibition reaction for intrinsic antioxidancy of high hydroxyl polyol esters:

HOO.+ROO.⇒ROOH+O$_2$

HOO.+RO.⇒ROH+O$_2$

The following reaction demonstrate the typical propagation reaction in the absence of antioxidants:

RH⇒R.(INITIATION)

R.+O$_2$⇒RO$_2$.(PROPAGATION)

RO$_2$.+RH⇒ROOH+R.(PROPAGATION)

ROOH⇒RO.+HO.(PROPAGATION)

RO.+RH⇒ROH+R.(PROPAGATION)

The impact of the high hydroxyl ester is to reduce the oxidation propensity for itself and hydrocarbons with which it is mixed or with which it has been combined through a permanent chemical bond. Consequently, the performance of the high hydroxyl ester can impact the oxidation of other additives, base stocks and higher molecular weight oligomers such as polymers.

Another preferred embodiment according to the present invention involves the increasing of the free radical scavenging capacity of antioxidants by grafting them onto polyhydroxy compounds such as mono-pentaerythritol, di-pentaerythritol, technical grade pentaerythritol, trimethylol propane, trimethylol ethane, neopentyl glycol or any other hydrocarbon such that the —CH$_2$OH group is produced either as a result of the grafting reaction or as a result of hydrolysis or other chemical reaction. A requirement of this embodiment is that the hydrocarbon portion of the compound whenever possible contain selected branched chains as designated herein.

According to this embodiment, the antioxidants are assumed to be free radical scavengers and are designated as AH, where H is assumed to be the active hydrogen atom in the free radical scavenging reaction:

AH+ROO.⇒ROOH+A.

An example of an enhanced efficiency antioxidant is the product of one mole of pentaerythritol and between 2 and 3 moles of 4-(p-2,6-di-t-butylphenol) butanoic acid. The antioxidant function of 2,6-di-t-butylphenol is well known. The presence of between 1 and 2 mole equivalents of free hydroxyl groups will increase the antioxidancy through the release of 2 mole equivalents of the hydroperoxyl moiety. The reaction of the hydroperoxyl moiety with free alkylhydroperoxyl radicals or alkylperoxyl radicals will result in the formation of more stable alkylhydrogen peroxides or alcohols and molecular oxygen.

The above mechanism shows how the oxidative degradation of the free —CH$_2$OH moiety results in the production of a reactive intermediate (i.e., HOO•), which scavenges alkoxyl and alkylperoxyl radicals. The product of the scavenging reactions are more stable intermediates and molecular oxygen. The key to the success of this chemistry is that the remaining portion of the compounds are relatively non-reactive in an oxidative environment. The present invention includes the use of aromatic antioxidants such as phenols and aromatic amines together with molecules containing a —CH$_2$OH moiety to produce an antioxidant complex that is relatively non-reactive in oxidative environments, except for the free radical scavenging reactions associated with AH or the reaction of —CH$_2$OH to produce HOO•. Antioxidants that are covered by this embodiment include the general class of phenols, aromatic amines, phosphites, and sulfur containing antioxidants, as well as any conventional antioxidant that functions as a free radical inhibitor or hydroperoxide decomposer.

Still another embodiment according to the present invention involves the modification of general antioxidants (AH) through grafting reactions that result in new antioxidants that produce free —CH$_2$OH groups upon hydrolysis and/or oxidation. An example of such an antioxidant is the same phenolic antioxidant described above in which the free hydroxyl group has been reacted with a facile leaving group. The leaving group could be facile under hydrolytic conditions to produce a free —CH$_2$OH moiety which could subsequently oxidize to produce the HOO. moiety. This grafting reaction results in new antioxidants formed from the reaction product comprising the reaction of YH with a polyol diacrylate, wherein Y is selected from the group consisting of: RS, R$_2$N, (RO)$_2$PHO, phenols and mixtures thereof; provided that RS is part of a sulfur containing antioxidant, R$_2$N is an aromatic amine or an alkyl amine antioxidant, and (RO)$_2$PHO is a phosphite antioxidant. Other antioxidants comprise phenols or combinations of any of the above antioxidants including metal containing antioxidants such as ZDDP.

Alternatively, the antioxidant system could be produced such that there are not any free hydroxyl groups nor any chemical bonds that would produce the —CH$_2$OH moiety upon hydrolysis, but which could produce, upon oxidation, the —CH$_2$OH moieties to yield HOO•. The antioxidants of the present invention that do not contain any free hydroxyl groups nor any chemical bonds that would produce the —CH$_2$OH moiety upon hydrolysis, but which do produce the —CH$_2$OH group upon oxidation, can be derived from the reaction product of:

(1) tris (hydroxymethyl)aminomethane and formaldehyde, thereby producing 1-aza-3,7-dioxa-bicyclo[3.3.0]octyl-5-methanol;
(2) tris (hydroxymethyl)aminomethane and cyclohexanone, thereby producing 2,2-pentamethylene-1,3-oxazolidine-4,4-dimethanol;
(3) tris (hydroxymethyl)arninomethane and a linear or branched carboxylic acid, thereby producing amides having the general formula:

R(C=O)NHC(CH$_2$OH)$_3$ wherein R is a linear or branched alkyl chain derived from the reaction product of a linear or branched acid with tris hydroxymethylaminomethane; and
(4) tris (hydroxymethyl)aminomethane and a linear or branched carboxylic acid, thereby producing substituted oxazolines having the general formula:

wherein R is a linear or branched alkyl chain derived from said linear or branched carboxylic acid.

The polyol ester composition of the present invention is preferably formed by reacting a polyhydroxyl compound with at least one acid (e.g., a branched and/or linear mono-carboxylic acid, diacid, or an aromatic acid). In the polyol ester composition, the polyol is preferably present in an excess of about 10 to 35 equivalent percent or more for the amount of acid used. The composition of the feed polyol is adjusted so as to provide the desired composition of the product ester.

The high hydroxyl esters formed in accordance with the present invention are typically resistant to high temperature oxidation with or without the use of conventional antioxidants such as V-81.

The acid is preferably a highly branched and/or linear mono-carboxylic acid such that the unconverted hydroxyl groups which are bonded to the resultant ester composition act similarly to an antioxidant such that it transfers a hydrogen atom to the unstable carbon radical which is produced when the ester molecule is under thermal stress, thereby effecting a "healing" of the radical (i.e., convert the carbon radical to a stable alcohol and oxygen). These unconverted hydroxyl groups which act as internal antioxidants, can substantially reduce or, in some instances, eliminate the need for the addition of costly antioxidants to the polyol ester composition. Moreover, esters having unconverted hydroxyl groups bonded thereto demonstrate substantially enhanced thermal/oxidative stability versus esters having similar amounts of antioxidants admixed therewith.

The esterification reaction is preferably conducted, with or without a catalyst, at a temperature in the range between about 140 to 250° C. and a pressure in the range between about 30 mm Hg to 760 mm Hg (3.999 to 101.308 kPa) for about 0.1 to 12 hours, preferably 1 to 8 hours. The stoichiometry in the reactor is variable, with the capability of vacuum stripping excess acid to generate the preferred final composition.

If the esterification reaction is conducted under catalytic conditions, then the preferred esterification catalysts are titanium, zirconium and tin catalysts such as titanium, zirconium and tin alcoholates, carboxylates and chelates. Selected acid catalysts may also be used in this esterification process. See U.S. Pat. No. 5,324,853 (Jones et al.), which issued on Jun. 28, 1994, and U.S. Pat. No. 3,056,818 (Werber), which issued on Oct. 2, 1962, both of which are incorporated herein by reference.

Alcohols

Among the alcohols which can be reacted with either the branched acid or branched and linear acid mixture are, by way of example, polyols (i.e., polyhydroxyl compounds) represented by the general formula:

$$R(OH)_n$$

wherein R is any aliphatic or cyclo-aliphatic hydrocarbyl group (preferably an alkyl) and n is at least 2. The hydrocarbyl group may contain from about 2 to about 20 or more carbon atoms, and the hydrocarbyl group may also contain substituents such as chlorine, nitrogen and/or oxygen atoms. The polyhydroxyl compounds generally may contain one or more oxyalkylene groups and, thus, the polyhydroxyl compounds include compounds such as polyetherpolyols. The number of carbon atoms (i.e., carbon number, wherein the term carbon number is used throughout this application) refers to the total number of carbon atoms $N_T$ in either the acid or alcohol, as the case may be.

The following alcohols are particularly useful as polyols: neopentyl glycol, 2,2-dimethylol butane, trimethylolethane, trimethylolpropane, trimethylolbutane, mono-pentaerythritol, technical grade pentaerythritol, di-pentaerythritol, tri-pentaerythritol, ethylene glycol, propylene glycol and polyalkylene glycols (e.g., polyethylene glycols, polypropylene glycols, polybutylene glycols, etc., and blends thereof such as a polymerized mixture of ethylene glycol and propylene glycol). The most preferred alcohols are technical grade (e.g., approximately 88% mono-, 10% di- and 1–2% tri-pentaerythritol) pentaerythritol, mono-pentaerythritol, di-pentaerythritol, neopentyl glycol and trimethylol propane.

Acids

Acids that are used in the preparation of high hydroxyl number esters affect their intrinsic antioxidancy. As noted, high hydroxyl number esters produce a relatively high concentration of HOO•, which is produced during oxidation of the —CH$_2$OH group. Because the —CH$_2$OH group is only one part of the high hydroxyl number ester, the rate at which the other part (i.e., the non-CH$_2$OH portion of the ester) oxidizes is important. Selected branched acids produce a slow rate of oxidation of this non-CH$_2$OH portion. When this portion oxidizes, the products include alkylperoxyl radical (ROO•), which are deleterious to performance. The key to success is an AH in which the rate of non-CH$_2$OH oxidation is slow relative to the rate of the —CH$_2$OH oxidation. The following groups of acids are preferred acids that impart or produce a relatively higher concentration of HOO. available to scavenge a higher number of alkyl radicals, ROO•. Accordingly, acids are $C_2$–$C_{20}$ acids, branched or linear. Preferred acids are selected from the following groups and are described in terms of the total number of carbon atoms ($N_T$) and the number of carbon atoms in the longest contiguous chain ($N_C$). $N_C$ is usually less than or equal to $N_T$, as $N_T$ includes carbons in methyl branches.

Group A

Carboxylic acid isomers having a carbon number $N_C$ ranging from 2 to 4, including straight chain acids, and branched acids such that the acid branches are derived from methyl or ethyl groups.

Group B

Carboxylic acid isomer having a carbon number $N_C$ ranging from 5 to 20 and:
  i. acids in which the penultimate carbon (i.e., $C_{m-1}$, where m is 20 and represents the maximum length of the longest contiguous carbon chain $N_C$) has 2 methyl branches
  ii. acids in which the penultimate carbon has one methyl group
  iii. acids in which the penultimate carbon is a methylene moiety.

For acids characterized in (i) above, it is preferred that:
  a. when branches are all gem dimethyl branches, these branches are at any position between $C_2$ and $C_{m-1}$;
  b. branches are monomethyl when there are gem dimethyl branches or a carbonyl group located two carbon positions from the point of attachment for the monomethyl group; and
  c. a monoethyl branch exists at position $C_2$.

For acids described in (ii), it is preferred that:
  a. a gem dimethyl group or a carbonyl group is attached 2 carbon positions from the point of attachment for the monomethyl group at the penultimate position.
  b. any other monomethyl substituents such that there is a gem dimethyl branch or a carbonyl group located 2 carbon positions away from the monomethyl point of attachment.
  c. any gem dimethyl groups, where these branches can be at any position between C-2 and C-($N_c$-2). This is independent of the preference identified in B above.
  d. a monoethyl branch at position C-2, with or without the preference A or B above.

For acids described in iii, it is preferred that:
  a. all gem dimethyl branches, where these branches can be at any position between C-2 and C-($N_c$-2).
  b. monomethyl branches when there are gem dimethyl branches or a carbonyl group located 2 carbon positions from the point of attachment for the monomethyl group.
  c. a monoethyl branch at position C-2, with or without the preference A or B above.

Branched Acids

The branched acid is preferably, but not necessarily, a mono-carboxylic acid which has a carbon number in the range between about $C_5$ to $C_{13}$, more preferably about $C_7$ to $C_{10}$ wherein methyl or ethyl branches are preferred as noted above. The mono-carboxylic acid is preferably at least one acid selected from the group consisting of: 2,2-dimethyl propionic acid (neopentanoic acid), neoheptanoic acid, neooctanoic acid, neononanoic acid, iso-hexanoic acid, neo-decanoic acid, 2-ethyl hexanoic acid (2EH), 3,5,5-trimethyl hexanoic acid (TMH). One especially preferred branched acid is 3,5,5-trimethyl hexanoic acid. The term "neo" as used herein refers to a trialkyl acetic acid, i.e., an acid which is triply substituted at the alpha carbon with alkyl groups. These alkyl groups are equal to or greater than $CH_3$ as shown in the general structure set forth herebelow:

wherein $R_1$, $R_2$, and $R_3$ are greater than or equal to $CH_3$ and not equal to hydrogen.

3,5,5-trimethyl hexanoic acid has the structure set forth herebelow:

Linear Acids

The mono- and/or di-carboxylic linear acids are any linear saturated alkyl carboxylic acid having a carbon number in the range between about $C_2$ to $C_{20}$, preferably $C_2$ to $C_{10}$.

Some examples of linear acids include acetic, n-propionic, n-pentanoic, n-heptanoic, n-octanoic, n-nonanoic, and n-decanoic acids. Selected polybasic acids include any $C_2$ to $C_{12}$ polybasic acids, e.g., adipic, azelaic, sebacic and dodecanedioic acids.

Aromatic Acids

The aromatic acids useful in accordance with the present invention include any acid of an aromatic antioxidant, such as phenols and aromatic amines. Of particular interest is 3-(p-2,6-di-t-butyl phenol) butanoic acid. ANTIOXIDANTS The free radical scavenging capacity of antioxidants can be increased by grafting such antioxidants onto polyols or any hydrocarbon such that the —$CH_2OH$ group is produced either as a result of the grafting reaction or as a result of hydrolysis or other chemical reaction. Antioxidants that are suitable for grafting may include, but not be limited to, the general class of phenols, aromatic amines, phosphites, sulfur containing antioxidants and any antioxidant that functions as a free radical inhibitor or hydroperoxide decomposer.

Antioxidant Boosters

The high hydroxyl polyol esters discussed above may be grafted to any other material to provide oxidation stability thereto. Such other materials may include mineral oils, polyol ester base stocks, polyalpha olefin base stocks, fuels, oligomers and polymers.

The process of synthesizing polyol ester compositions having significant unconverted hydroxyl groups according to the present invention typically follows the below equation:

wherein n is an integer having a value of at least 2, R is any aliphatic or cyclo-aliphatic hydrocarbyl group containing from about 2 to about 20 or more carbon atoms and, optionally, substituents such as chlorine, nitrogen and/or oxygen atoms, and R' is any branched aliphatic hydrocarbyl group having a carbon number in the range between about $C_4$ to $C_{12}$, more preferably about $C_6$ to Cg, wherein methyl or ethyl branches are preferred, and (i) is an integer having a value of between about 0 to n.

The reaction product from Equation 1 above can either be used by itself as a lubricant base stock or in admixture with other base stocks, such as mineral oils, highly refined mineral oils, polyalpha olefins (PAO), polyalkylene glycols (PAG), phosphate esters, silicone oils, diesters and polyol esters. When blended with other base stocks, the partial ester composition according to the present invention is preferably present in an amount of from about 1 to 50 wt. %, based on the total blended base stock, more preferably between about 1 to 25 wt. %, and most preferably between about 1 to 15 wt. %

The present invention also encompasses a metal carboxylic acid complex derived from a linear or branched acid and a metal such as titanium, silicon, aluminum, nickel, iron, copper, etc., which exhibits enhanced thermal/oxidative stability.

The polyol ester composition according to the present invention can be used in the formulation of various lubricants, such as, crankcase engine oils (i.e., passenger car motor oils, heavy duty diesel motor oils, and passenger car diesel oils), two-cycle engine oils, catapult oil, hydraulic fluids, drilling fluids, aircraft and other turbine oils, greases, gear oils, compressor oils, functional fluids and other industrial and engine lubrication applications. The lubricating oils contemplated for use with the polyol ester compositions of the present invention include both mineral and synthetic hydrocarbon oils of lubricating viscosity and mixtures thereof with other synthetic oils. The synthetic hydrocarbon oils include long chain alkanes such as cetanes and olefin polymers such as oligomers of hexene, octene, decene, and dodecene, etc. The other synthetic oils include (1) fully esterified ester oils, with no free hydroxyls, such as pentaerythritol esters of monocarboxylic acids having 2 to 20 carbon atoms, trimethylol propane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tri-pentaerythritol, with an aliphatic monocarboxylic acid containing from 1 to 20 carbon atoms, or mixtures of such acids.

In some of the lubricant formulations set forth above a solvent may be employed depending upon the specific application. Solvents that can be used include the hydrocarbon solvents, such as toluene, benzene, xylene, and the like.

The formulated lubricant according to the present invention preferably comprises about 60–99% by weight of at least one polyol ester composition of the present invention, about 1 to 20% by weight lubricant additive package, and about 0 to 20% by weight of a solvent. Alternatively, the base stock could comprise 1–50 wt % of at least one additional base stock selected from the group consisting of: mineral oils, highly refined mineral oils, alkylated mineral oils, poly alpha olefins, polyalkylene glycols, phosphate esters, silicone oils, diesters and polyol esters.

Crankcase Lubricating Oils

The polyol ester composition can be used in the formulation of crankcase lubricating oils (i.e., passenger car motor oils, heavy duty diesel motor oils, and passenger car diesel oils) for spark-ignited and compression-ignited engines. The additives listed below are typically used in such amounts so as to provide their normal attendant functions. Typical amounts for individual components are also set forth below. All the values listed are stated as mass percent active ingredient.

| ADDITIVE | MASS % (Broad) | MASS % (Preferred) |
|---|---|---|
| Ashless Dispersant | 0.1–20 | 1–8 |
| Metal detergents | 0.1–15 | 0.2–9 |
| Corrosion Inhibitor | 0–5 | 0–1.5 |
| Metal dihydrocarbyl dithiophosphate | 0.1–6 | 0.1–4 |
| Supplemental anti-oxidant | 0–5 | 0.01–1.5 |
| Pour Point Depressant | 0.01–5 | 0.01–1.5 |
| Anti-Foaming Agent | 0–5 | 0.001–0.15 |
| Supplemental Anti-wear Agents | 0–0.5 | 0–0.2 |
| Friction Modifier | 0–5 | 0–1.5 |
| Viscosity Modifier | 0.01–6 | 0–4 |
| Synthetic and/or Mineral Base Stock | Balance | Balance |

The individual additives may be incorporated into a base stock in any convenient way. Thus, each of the components can be added directly to the base stock by dispersing or dissolving it in the base stock at the desired level of concentration. Such blending may occur at ambient temperature or at an elevated temperature.

Preferably, all the additives except for the viscosity modifier and the pour point depressant are blended into a concentrate or additive package described herein as the additive package, that is subsequently blended into base stock to make finished lubricant. Use of such concentrates is conventional. The concentrate will typically be formulated to contain the additive(s) in proper amounts to provide the desired concentration in the final formulation when the concentrate is combined with a predetermined amount of base lubricant.

The concentrate is preferably made in accordance with the method described in U.S. Pat. No. 4,938,880. That patent describes making a pre-mix of ashless dispersant and metal detergents that is pre-blended at a temperature of at least about 100° C. Thereafter, the pre-mix is cooled to at least 85° C. and the additional components are added.

The final crankcase lubricating oil formulation may employ from 2 to 20 mass % and preferably 5 to 10 mass %, typically about 7 to 8 mass % of the concentrate or additive package with the remainder being base stock.

The ashless dispersant comprises an oil soluble polymeric hydrocarbon backbone having functional groups that are capable of associating with particles to be dispersed. Typically, the dispersants comprise amine, alcohol, amide, or ester polar moieties attached to the polymer backbone often via a bridging group. The ashless dispersant may be, for example, selected from oil soluble salts, esters, aminoesters, amides, imides, and oxazolines of long chain hydrocarbon substituted mono and dicarboxylic acids or their anhydrides; thiocarboxylate derivatives of long chain hydrocarbons; long chain aliphatic hydrocarbons having a polyamine attached directly thereto; and Mannich condensation products formed by condensing a long chain substituted phenol with formaldehyde and polyalkylene polyamine.

The viscosity modifier (VM) functions to impart high and low temperature operability to a lubricating oil. The VM used may have that sole function, or may be multifunctional.

Multifunctional viscosity modifiers that also function as dispersants are also known. Suitable viscosity modifiers are polyisobutylene, copolymers of ethylene and propylene and higher alpha-olefins, polymethacrylates, polyalkylmethacrylates, methacrylate copolymers, copolymers of an unsaturated dicarboxylic acid and a vinyl compound, inter polymers of styrene and acrylic esters, and partially hydrogenated copolymers of styrene/isoprene, styrene/butadiene, and isoprene/butadiene, as well as the partially hydrogenated homopolymers of butadiene and isoprene and isoprene/divinylbenzene.

Metal-containing or ash-forming detergents function both as detergents to reduce or remove deposits and as acid neutralizers or rust inhibitors, thereby reducing wear and corrosion and extending engine life. Detergents generally comprise a polar head with long hydrophobic tail, with the polar head comprising a metal salt of an acid organic compound. The salts may contain a substantially stoichiometric amount of the metal in which they are usually described as normal or neutral salts, and would typically have a total base number (TBN), as may be measured by ASTM D-2896, of from 0 to 80. It is possible to include large amounts of a metal base by reacting an excess of a metal compound such as an oxide or hydroxide with an acid gas such as carbon dioxide. The resulting overbased detergent comprises neutralized detergent as the outer layer of a metal base (e.g., carbonate) micelle. Such overbased detergents may have a TBN of 150 or greater, and typically from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450.

Dihydrocarbyl dithiophosphate metal salts are frequently used as anti-wear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt any basic or neutral zinc compound could be used but the oxides, hydroxides and carbonates are most generally employed. Commercial additives frequently contain an excess of zinc due to use of an excess of the basic zinc compound in the neutralization reaction.

Oxidation inhibitors or antioxidants reduce the tendency of base stocks to deteriorate in service which deterioration can be evidenced by the products of oxidation such as sludge and varnish-like deposits on the metal surfaces and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, ashless oil soluble phenates and sulfurized phenates, phosphosulfurized or sulfurized hydrocarbons, phosphorous esters, metal thiocarbamates, oil soluble copper compounds as described in US-A-4867890, and molybdenum containing compounds.

Friction modifiers may be included to improve fuel economy. Oil-soluble alkoxylated mono- and di-amines are well known to improve boundary layer lubrication. The amines may be used as such or in the form of an adduct or reaction product with a boron compound such as a boric oxide, boron halide, metaborate, boric acid or a mono-, di- or tri-alkyl borate.

Other friction modifiers are known. Among these are esters formed by reacting carboxylic acids and anhydrides with alkanols. Other conventional friction modifiers generally consist of a polar terminal group (e.g. carboxyl or hydroxyl) covalently bonded to an oleophillic hydrocarbon chain. Esters of carboxylic acids and anhydrides with alkanols are described in U.S. Pat. No. 4,702,850. Examples of other conventional friction modifiers are described by M. Belzer in the "Journal of Tribology" (1992), Vol. 114, pp. 675–682 and M. Belzer and S. Jahanmir in "Lubrication Science" (1988), Vol. 1, pp. 3–26. One such example is organo-metallic molybdenum.

Rust inhibitors selected from the group consisting of nonionic polyoxyalkylene polyols and esters thereof, polyoxyalkylene phenols, and anionic alkyl sulfonic acids may be used.

Copper and lead bearing corrosion inhibitors may be used, but are typically not required with the formulation of the present invention. Typically such compounds are the thiadiazole polysulfides containing from 5 to 50 carbon atoms, their derivatives and polymers thereof. Derivatives of 1,3,4 thiadiazoles such as those described in U.S. Pat. Nos. 2,719,125; 2,719,126; and 3,087,932; are typical. Other similar materials are described in U.S. Pat. Nos. 3,821,236; 3,904,537; 4,097,387; 4,107,059; 4,136,043; 4,188,299; and 4,193,882. Other additives are the thio and polythio sulfenamides of thiadiazoles such as those described in GB-1560830. Benzotriazoles derivatives also fall within this class of additives. When these compounds are included in the lubricating composition, they are preferably present in an amount not exceeding 0.2 wt % active ingredient.

A small amount of a demulsifying component may be used. A preferred demulsifying component is described in EP-330522. It is obtained by reacting an alkylene oxide with an adduct obtained by reacting a bis-epoxide with a polyhydric alcohol. The demulsifier should be used at a level not exceeding 0.1 mass % active ingredient. A treat rate of 0.001 to 0.05 mass % active ingredient is convenient.

Pour point depressants, otherwise known as lube oil flow improvers, lower the minimum temperature at which the fluid will flow or can be poured. Such additives are well known. Typical of those additives which improve the low temperature fluidity of the fluid are $C_8$ to $C_{18}$ dialkyl fumarate/vinyl acetate copolymers, polyalkylmethacrylates and the like.

Foam control can be provided by many compounds including an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and does not require further elaboration.

Two-cycle Engine Oils

The polyol ester composition can be used in the formulation of two-cycle engine oils together with selected lubricant additives. The preferred two-cycle engine oil is typically formulated using the polyol ester composition formed according to the present invention together with any conventional two-cycle engine oil additive package. The additives listed below are typically used in such amounts so as to provide their normal attendant functions. The additive package may include, but is not limited to, viscosity index improvers, corrosion inhibitors, oxidation inhibitors, coupling agents, dispersants, extreme pressure agents, color stabilizers, surfactants, diluents, detergents and rust inhibitors, pour point depressants, antifoaming agents, and anti-wear agents.

The two-cycle engine oil according to the present invention can employ typically about 75 to 85% base stock, about 1 to 5% solvent, with the remainder comprising an additive package.

Examples of the above additives for use in lubricants are set forth in the following documents which are incorporated herein by reference: U.S. Pat. No. 4,663,063 (Davis), which issued on May 5, 1987; U.S. Pat. No. 5,330,667 (Tiffany, III et al.), which issued on Jul. 19, 1994; U.S. Pat. No. 4,740, 321 (Davis et al.), which issued on Apr. 26, 1988; U.S. Pat.

No. 5,321,172 (Alexander et al.), which issued on Jun. 14, 1994; and U.S. Pat. No. 5,049,291 (Miyaji et al.), which issued on Sep. 17, 1991.

Catapult Oils

Catapults are instruments used on aircraft carriers at sea to eject the aircraft off of the carrier. The polyol ester composition can be used in the formulation of catapult oils together with selected lubricant additives. The preferred catapult oil is typically formulated using the polyol ester composition formed according to the present invention together with any conventional catapult oil additive package. The additives listed below are typically used in such amounts so as to provide their normal attendant functions. The additive package may include, but is not limited to, viscosity index improvers, corrosion inhibitors, oxidation inhibitors, extreme pressure agents, color stabilizers, detergents and rust inhibitors, antifoaming agents, anti-wear agents, and friction modifiers. These additives are disclosed in Klamann, "Lubricants and Related Products", *Verlag Chemie*, Deerfield Beach, Fla., 1984, which is incorporated herein by reference.

The catapult oil according to the present invention can employ typically about 90 to 99% base stock, with the remainder comprising an additive package.

Hydraulic Fluids

The polyol ester composition can be used in the formulation of hydraulic fluids together with selected lubricant additives. The preferred hydraulic fluids are typically formulated using the polyol ester composition formed according to the present invention together with any conventional hydraulic fluid additive package. The additives listed below are typically used in such amounts so as to provide their normal attendant functions. The additive package may include, but is not limited to, viscosity index improvers, corrosion inhibitors, boundary lubrication agents, demulsifiers, pour point depressants, and antifoaming agents.

The hydraulic fluid according to the present invention can employ typically about 90 to 99% base stock, with the remainder comprising an additive package.

Other additives are disclosed in U.S. Pat. No. 4,783,274 (Jokinen et al.), which issued on Nov. 8, 1988, and which is incorporated herein by reference.

Drilling Fluids

The polyol ester composition can be used in the formulation of drilling fluids together with selected lubricant additives. The preferred drilling fluids are typically formulated using the polyol ester composition formed according to the present invention together with any conventional drilling fluid additive package. The additives listed below are typically used in such amounts so as to provide their normal attendant functions. The additive package may include, but is not limited to, viscosity index improvers, corrosion inhibitors, wetting agents, water loss improving agents, bactericides, and drill bit lubricants.

The drilling fluid according to the present invention can employ typically about 60 to 90% base stock and about 5 to 25% solvent, with the remainder comprising an additive package. See U.S. Pat. No. 4,382,002 (Walker et al), which issued on May 3, 1983, and which is incorporated herein by reference.

Greases

The polyol ester composition can be used in the formulation of greases together with selected lubricant additives. The main ingredient found in greases is the thickening agent or gellant and differences in grease formulations have often involved this ingredient. Besides, the thickener or gellants, other properties and characteristics of greases can be influenced by the particular lubricating base stock and the various additives that can be used.

The preferred greases are typically formulated using the polyol ester composition formed according to the present invention together with any conventional grease additive package. The additives listed below are typically used in such amounts so as to provide their normal attendant functions. The additive package may include, lo but is not limited to, viscosity index improvers, oxidation inhibitors, extreme pressure agents, detergents and rust inhibitors, pour point depressants, metal deactivators, anti-wear agents, and thickeners or gellants.

The grease according to the present invention can employ typically about 80 to 95% base stock and about 5 to 20% thickening agent or gellant, with the remainder comprising an additive package.

Typical thickening agents used in grease formulations include the alkali metal soaps, clays, polymers, asbestos, carbon black, silica gels, polyureas and aluminum complexes. Soap thickened greases are the most popular with lithium and calcium soaps being most common. Simple soap greases are formed from the alkali metal salts of long chain fatty acids with lithium 12-hydroxystearate, the predominant one formed from 12-hydroxystearic acid, lithium hydroxide monohydrate and mineral oil. Complex soap greases are also in common use and comprise metal salts of a mixture of organic acids. One typical complex soap grease found in use today is a complex lithium soap grease prepared from 12-hydroxystearic acid, lithium hydroxide monohydrate, azelaic acid and mineral oil. The lithium soaps are described and exemplified in may patents including U.S. Pat. No. 3,758,407 (Harting), which issued on Sep. 11, 1973; U.S. Pat. No. 3,791,973 (Gilani), which issued on Feb. 12, 1974; and U.S. Pat. No. 3,929,651 (Murray), which issued on Dec. 30, 1975, all of which are incorporated herein by reference together with U.S. Pat. No. 4,392,967 (Alexander), which issued on Jul. 12, 1983.

A description of the additives used in greases may be found in Boner, "Modern Lubricating Greases", 1976, Chapter 5, which is incorporated herein by reference, as well as additives listed above in the other products.

Compressor Oils

The polyol ester composition can be used in the formulation of compressor oils together with selected lubricant additives. The preferred compressor oil is typically formulated using the polyol ester composition formed according to the present invention together with any conventional compressor oil additive package. The additives listed below are typically used in such amounts so as to provide their normal attendant functions. The additive package may include, but is not limited to, oxidation inhibitors, additive solubilizers, rust inhibitors/metal passivators, demulsifying agents, and anti-wear agents.

The compressor oil according to the present invention can employ typically about 80 to 99% base stock and about 1 to 15% solvent, with the remainder comprising an additive package.

The additives for compressor oils are also set forth in U.S. Pat. No. 5,156,759 (Culpon, Jr.), which issued on Oct. 20, 1992, and which is incorporated herein by reference.

It is extremely important in many lubricant applications such as aircraft turbine oils to provide a lubricant product which is thermally/oxidatively stable. One means of measuring relative thermal/oxidative stability in lubric ants is via high pressure differential scanning calorimetry (HPDSC). In this test, the sample is heated to a fixed temperature and held there under a pressure of air (or oxygen) and the time to onset of decomposition is measured. The longer the time to decomposition, the more stable the sample. In all cases described hereafter, the conditions are as follows unless specifically noted otherwise: 220° C., 3.445 MPa (500 psi) air (i.e., 0.689 MPa (100 psi) oxygen and 2.756 MPa (400 psi) nitrogen), and the addition of 0.5 wt. % dioctyl diphenyl amine (Vanlub®-81®) as an antioxidant.

Figure 1:
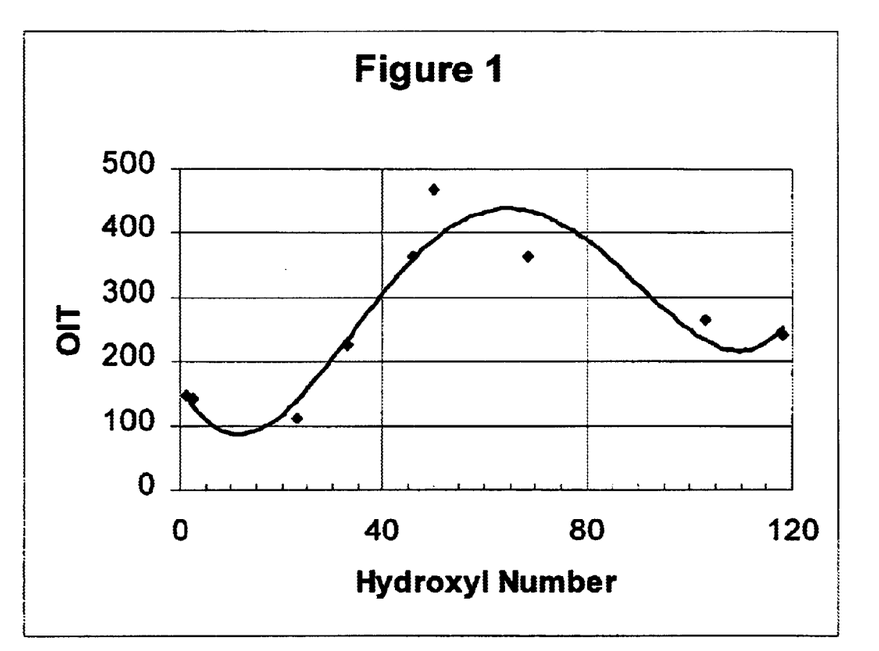
FIG. 1 is a graph plotting HPDSC results versus hydroxyl number for Tech PE/TMH.

As illustrated in FIG. 1, as the hydroxyl number increases (i.e., a fully esterified ester), the oxidative induction time increases, thereafter, less rapidly reduces. It is believed that as the hydroxyl number increases beyond substantially esterified (i.e., OH number greater than about 30) a higher concentration of hydroperoxyl radicals HOO• is formed and may function to scavenge a relatively greater number of alkyl radicals ROO. that are produced in the oxidation process. However, above a preferable range (i.e., OH number greater than about 180) the hydroperoxyl radicals, HOO•, become oxidative initiators as well as alkyl radical scavengers, and oxidative stability declines.

The data set forth below in Table 1 indicate that there is considerable room for improving the thermal/oxidative performance of polyol esters as measured by the HPDSC test. In particular, it should be noted that esters of 3,5,5-trimethyl hexanoic acid and 2,2-dimethylpropionic acid (i.e., neopentanoic (neoC$_5$)) are particularly stable under the HPDSC test.

TABLE 1

| Sample Number | Ester* | HPDSC Decomposition Time, Min. |
|---|---|---|
| 1 | TMP/n-C$_9$ | 14.2 |
| 2 | TechPE/n-C$_9$ | 14.7 |
| 3 | TMP/TMH | 119 |
| 4 | TechPE/TMH | 148 |
| 5 | MPE/TMH | 143 |
| 6 | TMP/n-C$_5$ | 51.9 |

TABLE 1-continued

| Sample Number | Ester* | HPDSC Decomposition Time, Min. |
|---|---|---|
| 7 | 50% TMP/TMH and 50% TMP/n-C$_5$ | 65.7 |
| 8 | MPE/TMH/neo-C$_5$ | 168 |

*with 0.5 wt. % dioctyldiphenylamine antioxidant n-C$_9$ is a linear normal C$_9$ acid.
TechPE is technical grade pentaerythritol (i.e., 88% mono-, 10% di- and 1–2% tri-pentaerythritol).
MPE is mono-pentaerythritol.
n-C$_5$ is a linear normal C$_5$ acid.
TMH is 3,5,5-trimethyl hexanoic acid.
neo-C$_5$ is 2,2-dimethyl propionic acid.

EXAMPLE 1

Certain polyol esters containing at least 1 mole % unconverted hydroxyl groups show dramatic enhancements in thermal/oxidative performance in the HPDSC test. These esters contain specific types of branching and the enhancement is seen for both trimethylol propane (TMP) and pentaerythritol (both mono grade and technical grade) esters. Table 2 below summarizes the results obtained by the present inventors.

TABLE 2

| HPDSC Sample Number | Ester | Hydroxyl No. | Decomposition Time, Min. |
|---|---|---|---|
| 1 | TMP/2EH | 20 | 30.1 |
| 2 | TMP/2EH | 64.0 | 225.3 |
| 3 | TMP/2EH | 75.0 | 125.3 |
| 4 | MPE/2EH | 12.1 | 24.4 |
| 5 | MPE/2EH | 63.8 | 183.5 |
| 6 | TechPE/2EH | 3.6 | 17.5 |
| 7 | TechPE/TMH | <10 | 148 |
| 8 | TechPE/TMH | 86 | 268 |
| 9 | TechPE/TMH | 68.5 | 364 |
| 10 | TechPE/TMH | >50 | 468 |
| 11 | TMP/7810 | 0.2 | 26.1 |
| 12 | TMP/7810 | 25.7 | 21.3 |
| 13 | TMP/7810 | 26.8 | 22.9 |
| 14 | TMP/7810 | 43.5 | 21.3 |
| 15 | TMP/7810 | 73.8 | 26.5 |

Hydroxyl Number is measured in mg KOH/gram sample using a conventional near infrared technique.
2EH is 2 ethyl hexanoic acid.
TechPE is technical grade pentaerythritol (i.e., 88% mono-, 10% di- and 1–2% tri-pentaerythritol).
MPE is mono-pentaerythritol.
TMH is 3,5,5-trimethyl hexanoic acid.
TMP is trimethylol propane.
7810 is a blend of 37 mole % of a n-C$_7$ acid and 63 mole % of a mixture of 3–5 mole % n-C$_6$ acid, 48–58 mole % n-C$_8$ acid, 36–42 mole % n-C$_{10}$ acid, and 0.5–1.0 mole % n-C$_{12}$ acid.

The results set forth above in Table 2 and FIG. 1 demonstrate that when all of the initially added antioxidant (Vanlube®-81) is consumed, that the ester radicals are not healed and uncontrolled decomposition occurs at lower times as shown in sample numbers 1, 4 and 6 which have small amounts of unconverted hydroxyl groups, i.e., hydroxyl number less than about 30, as well in the polyol esters formed from linear acids regardless of amount of unconverted —CH$_2$OH groups present (see samples numbers 11–15). With certain branched esters such as sample numbers 2, 3, and 6–10 above, the unconverted —CH$_2$OH group (i.e., the only molecular change from the full ester) is capable of producing HOO•, which transfers its hydrogen to the RO• and ROO• radicals so as to create more stable intermediates, thereby acting as an additional antioxidant. With the linear acid esters set forth in the above sample numbers 11–15, the rate of oxidation of the alkyl chain occurs faster than the rate of •OOH production and consequently the high hydroxyl ester does not inhibit oxidation.

EXAMPLE 2

The data set forth below in Table 3 demonstrate that polyol ester compositions having unconverted hydroxyl groups which are formed from polyols and branched acids in accordance with the present invention exhibit intrinsic antioxidant properties.

TABLE 3

| HPDSC Sample Number | Ester | Hydroxyl Number | Decomposition Time, Min. |
|---|---|---|---|
| 1 | TechPE/TMH | greater than 50 | 468 with 0.5% V-81 |
| 2 | TechPE/TMH | greater than 50 | 58.3 with no V-81 |
| 3 | TechPE/L9 | less than 5 | 16.9 with 0.5% V-81 |
| 4 | Tech PE/TMH | less than 5 | 148 with 0.5% V-81 |
| 5 | Tech PE/TMH | less than 5 | 3.14 with no V-81 |

V-81 is dioctyl diphenyl amine.
TechPE is technical grade pentaerythritol (i.e., 88% mono-, 10% di- and 1–2% tri-pentaerythritol).
TMH is 3,5,5-trimethyl hexanoic acid.
L9 is blend of 62–70 mole % linear $C_9$ acid and 30–38 mole % branched $C_9$ acid.

The results in Table 3 above demonstrate that polyol esters with elevated levels of unconverted hydroxyl groups (i.e., sample numbers 1 and 2) result in enhanced oxidative induction times versus conventional polyol esters which do not have any significant amount of free or unconverted hydroxyl groups. Moreover, combining these unique polyol esters with an antioxidant such as V-81 significantly extends the time required for decomposition (see sample no. 1). Although the time for decomposition was reduced when this polyol ester did not include any added antioxidant, it still took approximately 3½ times longer to decompose versus a conventional $C_9$ acid polyol ester which had an antioxidant additive (i.e., 58.3 minutes (sample 2) versus 16.9 minutes (sample 3)). Furthermore, Samples 4 and 5 demonstrate that decomposition of the polyol ester compositions having a hydroxyl number less than 5 occurs much more rapidly compared to polyol ester compositions of the same acid and polyol having a hydroxyl number greater than 50 (e.g., Samples 1 and 2) regardless of whether or not an antioxidant is admixed with the respective polyol ester composition. This clearly demonstrates that synthesizing a polyol ester composition having unconverted hydroxyl groups disposed about the carbon chain of the polyol ester provides enhanced thermal/oxidative stability to the resultant product, as measured by HPDSC. Finally, a comparison of Sample Nos. 2 and 5, wherein no antioxidant was used, clearly establishes the antioxidant properties of the polyol ester of technical grade pentaerythritol and 3,5,5-trimethyl hexanoic acid having substantial amounts of unconverted hydroxyl group bonded which has an HPDSC of 58.3 minutes versus the same polyol ester with little or no unconverted hydroxyl groups which has an HPDSC of 3.14 minutes.

EXAMPLE 3

Data set forth below in Table 4 demonstrate that polyol esters with unconverted hydroxyl groups (i.e., unconverted hydroxyl groups) formed from polyols and branched acids according to the present invention are also capable of enhancing the thermal/oxidative stability when blended with other hydrocarbon base stocks such as poly alpha olefins (PAO).

TABLE 4

| Sample Number | Base Stock Composition | Hydroxyl Number* | HPDSC Decomposition Time, Min.** |
|---|---|---|---|
| 1 | 95% PAO6 and 5% TechPE/TMH | <5 | 12.89 |
| 2 | 90% PAO6 and 10% TechPE/TMH | <5 | 13.52 |
| 3 | 75% PAO6 and 25% TechPE/TMH | <5 | 17.03 |
| 4 | 95% PAO6 and 5% MPE/TMH | 68.5 | 22.57 |
| 5 | 90% PAO6 and 10% MPE/TMH | 68.5 | 53.68 |
| 6 | 75% PAO6 and 25% MPE/TMH | 68.5 | 108.86 |

PAO6 is a 1-decene oligomer.
*Hydroxyl Number is measured in mg KOH/gram sample and is the hydroxyl number of the ester-containing portion of the blend.
**Denotes that the HPDSC measurement was conducted at 190° C. and 3.445 MPa in the presence of 0.5% Vanlube ®-81 additive (i.e., dioctyl diphenyl amine).
TechPE is technical grade pentaerythritol (i.e., 88% mono-, 10% di- and 1–2% tri-pentaerythritol).
MPE is mono-pentaerythritol.
TMH is 3,5,5-trimethyl hexanoic acid.

Figure 2:
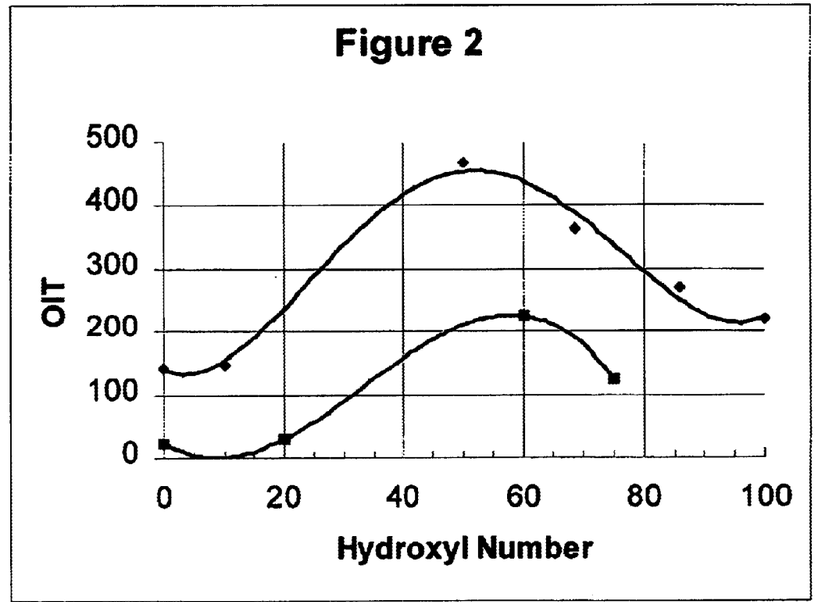
FIG. 2 is a graph plotting HPDSC results versus hydroxyl number for various polyol esters having unconverted hydroxyl groups bonded thereto.

The results set forth above in Table 4 and FIG. 2 demonstrate that polyol ester compositions with at least 10% unconverted hydroxyl content having hydroxyl numbers greater than about 30 (i.e., sample numbers 8–12) bring about enhanced thermal/oxidative stability as measured by HPDSC when blended with hydrocarbon base stocks such as poly alpha olefins.

EXAMPLE 4

Data set forth below in Table 5 demonstrate that polyol esters with unconverted hydroxyl groups formed from polyols and branched acids according to the present invention and which have been admixed with 0.5% Vanlube® 81 (an antioxidant) are capable of retarding the onset of thermal-loxidative degradation as measured by HPDSC. The below samples where run at 3.445 MPa (500 psi) air (i.e., 0.689 MPa (100 psi) oxygen and 2.756 MPa (400 psi) nitrogen.

TABLE 5

| Sample | Hydrocarbon | Ester | Ratio | Temp. (° C.) | Hydroxyl Number | HPDSC (minutes) |
|---|---|---|---|---|---|---|
| 1 | SN150 | MPE/2EH | 95/5 | 190 | 63.5 | 14.53 |
| 2 | SN150 | MPE/2EH | 90/10 | 190 | 63.5 | 22.41 |
| 3 | SN150 | MPE/2EH | 75/25 | 190 | 63.5 | 31.94 |
| 4 | SN150 | MPE/TMH | 95/5 | 190 | 68.5 | 16.98 |
| 5 | SN150 | MPE/TMH | 90/10 | 190 | 68.5 | 17.58 |
| 6 | SN150 | MPE/TMH | 75/25 | 190 | 68.5 | 57.18 |

SN150 is a low sulfur, neutralized, saturated, linear hydrocarbon having between 14 to 34 carbon atoms.
TMH is 3,5,5-trimethyl hexanoic acid.
2EH is 2 ethyl hexanoic acid.
MPE is monopentaerythritol.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A lubricant having a major amount of lubricating oil and a minor amount of an antioxidant comprising the reaction product of tris (hydroxymethyl) aminomethane and a linear or branched carboxylic acid, thereby producing substituted oxazolines having the general formula:

wherein R is a linear or branched alkyl chain derived from said linear or branched carboxylic acid.

2. The lubricant of claim 1 wherein said antioxidant has a hydroxyl number of greater than about 30 and less than about 180.

3. The lubricant of claim 1 wherein said antioxidant has a hydroxyl number of greater than about 50 and less than about 120.

4. The lubricant of claim 1 wherein said antioxidant has a hydroxyl number of greater than about 70 and less than about 100.

5. The lubricant of claim 1 wherein said carboxylic acid comprises about 50% or more of a branched carboxylic acid.

6. The lubricant of claim 5 wherein said branched carboxylic acid is 2-methyl-propanoic acid.

7. The lubricant of claim 5 wherein said branched carboxylic acid is further characterized as having a carbon number from about 5 to about 20, wherein said carboxylic acid has at least one methyl group located at the penultimate carbon position $C_{m-1}$.

8. The lubricant of claim 7 wherein branches of the branched carboxylic acid are characterized as dimethyl branches, said dimethyl branches being located at any position between, and including, $C_2$ and $C_{m-1}$.

9. The lubricant of claim 7 wherein the branched carboxylic acid has a methylene moiety at the penultimate carbon position.

10. The lubricant of claim 7 wherein when the penultimate carbon position has one methyl group, another methyl group can be located on the contiguous chain such that there is one of a gem dimethyl group or carbonyl group located two carbon positions from the another methyl group.

11. The lubricant of claim 1 further comprising a monoethyl branch located at position 2 of the contiguous carbon chain.

* * * * *